(12) United States Patent
Wang et al.

(10) Patent No.: US 7,359,048 B2
(45) Date of Patent: Apr. 15, 2008

(54) RAMAN SIGNAL-ENHANCING STRUCTURES AND DEVICES

(75) Inventors: Shih-Yuan Wang, Palo Alto, CA (US); R. Stanley Williams, Palo Alto, CA (US); Raymond G. Beausoleil, Palo Alto, CA (US); Theodore I. Kamins, Palo Alto, CA (US); Zhiyong Li, Palo Alto, CA (US); Wei Wu, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 183 days.

(21) Appl. No.: 11/413,910

(22) Filed: Apr. 28, 2006

(65) Prior Publication Data

US 2007/0252982 A1 Nov. 1, 2007

(51) Int. Cl.
*G01J 3/44* (2006.01)
*G01N 21/65* (2006.01)

(52) U.S. Cl. .................. 356/301; 356/454; 356/519

(58) Field of Classification Search ............ 356/301
See application file for complete search history.

(56) References Cited

U.S. PATENT DOCUMENTS

| 6,781,690 | B2 | 8/2004 | Armstrong et al. |
| 6,867,900 | B2 * | 3/2005 | Weisbuch et al. ........... 359/321 |
| 6,970,239 | B2 | 11/2005 | Chan et al. |
| 6,989,897 | B2 | 1/2006 | Chan et al. |
| 7,307,719 | B2 * | 12/2007 | Wang et al. ................. 356/301 |
| 2003/0059820 | A1 | 3/2003 | Vo-Dinh |
| 2004/0150818 | A1 | 8/2004 | Armstrong et al. |
| 2005/0024634 | A1 | 2/2005 | Barker et al. |
| 2005/0084912 | A1 | 4/2005 | Poponin |
| 2005/0110990 | A1 | 5/2005 | Koo et al. |
| 2005/0206892 | A1 | 9/2005 | Wang et al. |
| 2007/0086001 | A1 * | 4/2007 | Islam et al. ................. 356/301 |
| 2007/0252983 | A1 * | 11/2007 | Tong et al. .................. 356/301 |

OTHER PUBLICATIONS

Srituravanich, W., et al., "Sub-100 nm lithography using ultrashort wavelength of surface plasmons," J. Vac. Sci. Technol. B, vol. 22, No. 6, pp. 3475-3478, Nov./Dec. 2004.

* cited by examiner

*Primary Examiner*—F. L. Evans

(57) ABSTRACT

Raman systems include a radiation source, a radiation detector, and a Raman device or signal-enhancing structure. Raman devices include a tunable resonant cavity and a Raman signal-enhancing structure coupled to the cavity. The cavity includes a first reflective member, a second reflective member, and an electro-optic material disposed between the reflective members. The electro-optic material exhibits a refractive index that varies in response to an applied electrical field. Raman signal-enhancing structures include a substantially planar layer of Raman signal-enhancing material having a major surface, a support structure extending from the major surface, and a substantially planar member comprising a Raman signal-enhancing material disposed on an end of the support structure opposite the layer of Raman signal-enhancing material. The support structure separates at least a portion of the planar member from the layer of Raman signal-enhancing material by a selected distance of less than about fifty nanometers.

25 Claims, 8 Drawing Sheets

RAMAN SIGNAL-ENHANCING STRUCTURES AND DEVICES

FIELD OF THE INVENTION

The present invention relates to Raman spectroscopy. More particularly, the invention relates Raman signal-enhancing structures for enhancing the Raman-scattered radiation that is scattered by an analyte, Raman devices that include Raman signal-enhancing structures coupled to tunable resonant cavities, and Raman spectroscopy systems including such Raman signal-enhancing structures and devices.

BACKGROUND OF THE INVENTION

Raman spectroscopy is a technique for analyzing molecules or materials. In conventional Raman Spectroscopy, an analyte (or sample) that is to be analyzed is irradiated with high intensity monochromatic electromagnetic radiation provided by a radiation source, such as a laser. An electromagnetic radiation detector detects radiation that is scattered by the analyte. The characteristics of the scattered radiation provide information relating to the analyte.

Conventional Raman spectroscopy systems typically include an electromagnetic radiation source that is configured to emit incident electromagnetic radiation, an analyte stage on which an analyte may be positioned, and an electromagnetic radiation detector. The radiation detector is configured to detect at least a portion of scattered radiation that is scattered by the analyte. Raman spectroscopy systems also typically include various optical components positioned between the radiation source and the analyte stage, and between the analyte stage and the radiation detector. Such optical components may include lenses, filters, and apertures.

The radiation source may be a commercially available laser. The wavelength or wavelengths of incident electromagnetic radiation that may be emitted by the electromagnetic radiation source typically are within or near the visible region of the electromagnetic radiation spectrum.

The radiation detector receives and detects at least a portion of the scattered radiation that is scattered by an analyte disposed on the analyte stage. The detector includes a device for determining the wavelength of the scattered radiation (for example, a monochromator) and a device for determining the intensity of the scattered radiation (for example, a photomultiplier). Typically, the scattered radiation is scattered in all directions relative to the analyte stage.

Optical components positioned between the radiation source and the analyte stage are used to collimate, filter, or focus the incident radiation before the incident radiation impinges on the analyte stage. Optical components positioned between the analyte stage and the radiation detector are used to collimate, filter, or focus the scattered radiation.

An analyte is provided on an analyte stage of a Raman spectroscopy system and irradiated with incident radiation emitted by a radiation source to perform Raman spectroscopy using a Raman spectroscopy system. As the incident radiation impinges on the analyte, at least some of the incident radiation will be scattered by the analyte. A majority of the photons of the incident radiation that impinge on the analyte are elastically scattered by the analyte. In other words, the scattered photons have the same energy, and thus the same wavelength, as the incident photons. This elastic scattering of photons is termed "Rayleigh scattering," and radiation consisting of these elastically scattered photons is termed "Rayleigh scattered radiation" or "Rayleigh radiation."

The Rayleigh scattering process can be further described with reference to the simplified Jablonski diagram shown schematically in FIG. 1, which illustrates various energy levels of a hypothetical analyte. In FIG. 1, energy levels of the analyte are represented as horizontal lines. As seen therein, the ground state energy level (the lowest energy level) is shown at the bottom of the diagram, excited vibrational energy states are shown just above the ground state, excited electronic energy states are shown at the top of the diagram, and virtual excited states are shown between the excited electronic states and the excited vibrational states. As seen in FIG. 1, Rayleigh scattering typically involves absorption of a single photon of the incident radiation by the analyte, which causes the analyte to transition from the ground state to a virtual state followed by relaxation to the ground state. As the analyte relaxes to the ground state, the analyte emits a photon of scattered radiation that has energy equal to that of the photon of the incident radiation. In this manner, the photon of the incident radiation is considered to have been elastically scattered.

In addition to the Rayleigh scattering of photons, a very small fraction of the photons of the incident radiation may be inelastically scattered by the analyte. Raman-scattered radiation is also emitted from the analyte. Typically, only about 1 in $10^7$ of the photons of the incident radiation is inelastically scattered by the analyte. These inelastically scattered photons have a different wavelength than the photons of the incident radiation. This inelastic scattering of photons is termed "Raman scattering," and radiation consisting of Raman-scattered photons is termed "Raman-scattered radiation" or "Raman radiation." The photons of the Raman-scattered radiation can have wavelengths less than, or more typically, greater than the wavelength of the photons of the incident radiation.

When a photon of the incident radiation collides with the analyte, energy can be transferred from the photon to the analyte or from the analyte to the photon. When energy is transferred form the photon of the incident radiation to the analyte, the Raman-scattered photon will have a lower energy and a corresponding longer wavelength than the incident photon. These Raman-scattered photons having lower energy than the incident photons are collectively referred to in Raman spectroscopy as the "Stokes radiation." As seen in FIG. 1, 1st order Stokes Raman scattering typically involves absorption of a single photon of the incident radiation by the analyte, which causes the analyte to transition from a first energy state (for example, the ground state) to an excited virtual state. The analyte then relaxes to an excited vibrational state of higher energy than the first energy state. As the analyte relaxes to the excited vibrational state, the analyte emits a photon of scattered radiation that has less energy (and a longer wavelength) than the photon of the incident radiation. In this manner, the photon of the incident radiation is considered to have been inelastically scattered.

When energy is transferred from the analyte to a Raman-scattered photon, the Raman-scattered photon will have a higher energy and a corresponding shorter wavelength than the photon of the incident radiation. These Raman-scattered photons, which have higher energy than the incident photons, are collectively referred to in Raman spectroscopy as the "anti-Stokes radiation." As seen in FIG. 1, 1st order anti-Stokes Raman scattering typically involves absorption of a single photon of the incident radiation by the analyte, which causes the analyte to transition from an excited vibrational energy state to an excited virtual state. The analyte then relaxes to a lower energy state (for example, the ground state) than the excited vibrational energy state. As the analyte relaxes to the lower energy state, the analyte emits a photon of scattered radiation that has more energy (and a shorter wavelength) than the photon of the incident radiation. In this manner, the photon of the incident radiation is considered to have been inelastically scattered.

The shift in energy (wavelength, frequency, or wave number) of the Raman-scattered photons in relation to the Rayleigh scattered photons is known as the "Raman shift."

Raman scattering primarily involves a one photon excitation—one photon relaxation process. These Raman scattering processes are often referred to as "1st order" Raman scattering processes. However, multiple photon excitation—single photon relaxation processes are also observed and are referred to as "hyper Raman scattering" processes. Two photon excitation—one photon relaxation scattering processes are referred to as "2nd order" hyper Raman scattering processes, three-photon excitation—one photon relaxation processes are referred to as "3rd order" Raman scattering processes, etc. These higher order Raman scattering processes are often referred to as "harmonics."

In 2nd order scattering processes, a molecule of the analyte in an initial energy state absorbs the energy from two photons of the incident radiation causing an energy transition in the analyte to a virtual excited state, followed by relaxation to a final energy state and emission of a single scattered photon. If the final energy state is the same as the initial energy state, the scattering process is referred to as hyper Raleigh scattering. If the final energy state is higher than the initial energy state, the scattering process is referred to as 2nd order Stokes hyper Raman scattering. Finally, if the final energy state is lower than the initial energy state, the scattering process is referred to as 2nd order anti-Stokes hyper Raman scattering. The Stokes and anti-Stokes 2nd order hyper Raman scattering processes are also represented in the Jablonski diagram shown in FIG. 1.

Information may be obtained from hyper Raman-scattered radiation that cannot be obtained from 1st order Raman-scattered radiation. In particular, vibrational information may be suppressed in Raman-scattered radiation due to symmetry issues, thereby resulting in what are often referred to as "silent modes." These silent modes may not be suppressed in the hyper Raman-scattered radiation.

When an analyte is irradiated with incident radiation, the scattered radiation may include Raman-scattered radiation, which may comprise 1st order Raman-scattered radiation (Stokes and anti-Stokes) and higher order hyper Raman-scattered radiation (Stokes and anti-Stokes), in addition to Rayleigh scattered radiation. The Raman-scattered radiation that is scattered by the analyte (including the hyper Raman-scattered radiation) is often referred to as the "Raman signal."

The Raman signal is detected using the radiation detector. The wavelengths and corresponding intensity of the Raman-scattered radiation may be determined and used to provide a Raman spectral graph. Analytes generate unique Raman spectral graphs. The unique Raman spectral graph obtained by performing Raman spectroscopy can be used to obtain information relating to the analyte including, but not limited to, the identification of an unknown analyte, or the determination of physical and chemical characteristics of a known analyte.

The number of Raman-scattered photons that are scattered by an analyte is extremely small relative to the number of Rayleigh scattered photons, and the number of hyper Raman-scattered photons is even smaller than the number of 1st order Raman-scattered photons. Typical radiation detectors are capable of detecting the high-intensity Rayleigh scattered radiation in addition to the low-intensity Raman-scattered radiation. The detection of the Raman-scattered radiation may be difficult due to the high intensity of the Rayleigh scattered radiation. To overcome this difficulty, a radiation filter may be positioned between the analyte stage and the detector to prevent the Rayleigh scattered radiation from being detected by the detector, thus allowing only the Raman-scattered radiation to be received by the detector. Commercially available notch filters may be used for such purposes.

After removal of the Rayleigh scattered radiation, the various wavelengths of Raman-scattered radiation typically are spatially separated using a diffraction grating. The separated wavelengths of Raman-scattered radiation typically are detected or imaged simultaneously using a charge coupled device (CCD) array. Alternatively, the wavelengths of Raman-scattered radiation may be detected using a photomultiplier tube (PMT).

Surface-enhanced Raman spectroscopy (SERS) is a technique that allows for enhancement of the intensity of the Raman-scattered radiation relative to conventional Raman spectroscopy (i.e., the number of Raman-scattered photons that are scattered by an analyte). In SERS, the analyte typically is adsorbed onto or placed adjacent to what is often referred to as a SERS-active structure. SERS-active structures typically include a metal surface or structure. Interactions between the analyte and the metal surface may cause an increase in the intensity of the Raman-scattered radiation.

Several types of metallic structures have been employed in SERS techniques to enhance the intensity of Raman-scattered radiation that is scattered by an analyte. Some examples of such structures include electrodes in electrolytic cells, metal colloid solutions, and metal substrates such as a roughened metal surface or metal "islands" formed on a substrate. For example, it has been shown that adsorbing analyte molecules onto or near a specially roughened metal surface of gold or silver can enhance the Raman scattering intensity by factors of between $10^3$ and $10^6$.

Raman spectroscopy recently has been performed employing metal nanoparticles, such as nanometer scale needles, particles, and wires, as opposed to a simple roughened metallic surface. This process will be referred to herein as nano-enhanced Raman spectroscopy (NERS). Structures comprising nanoparticles that are used to enhance the intensity of Raman-scattered radiation may be referred to as NERS-active structures. The intensity of the Raman-scattered radiation that is scattered by an analyte adsorbed on such a NERS-active structure can be increased by factors as high as $10^{16}$.

BRIEF SUMMARY OF THE INVENTION

In one aspect, the present invention includes a Raman device having a Raman signal-enhancing structure coupled to a tunable resonant cavity and configured to be irradiated by at least a portion of electromagnetic radiation that is resonating within the tunable resonant cavity. The tunable resonant cavity includes a first reflective member, a second reflective member, and an electro-optic material disposed between the first reflective member and the second reflective member. The electro-optic material exhibits a refractive index that varies in response to an applied electrical field.

In another aspect, the present invention includes a Raman system including a radiation source configured to emit electromagnetic radiation and a radiation detector configured to detect Raman-scattered radiation that is scattered by an analyte. The Raman system further includes a Raman device having a Raman signal-enhancing structure coupled to a tunable resonant cavity and configured to be irradiated by at least a portion of electromagnetic radiation that is resonating within the tunable resonant cavity. The tunable resonant cavity includes a first reflective member, a second reflective member, and an electro-optic material disposed between the first reflective member and the second reflective member. The electro-optic material exhibits a refractive index that varies in response to an applied electrical field.

In yet an additional aspect, the present invention includes a Raman signal-enhancing structure. The Raman signal-enhancing structure includes a substantially planar layer of Raman signal-enhancing material having a major surface, a support structure extending from the major surface of the layer of Raman signal-enhancing material, and a substantially planar member comprising a Raman signal-enhancing material disposed on an end of the support structure opposite the layer of Raman signal-enhancing material. The support structure separates at least a portion of the planar member from the layer of Raman signal-enhancing material by a selected distance of less than about fifty (50) nanometers.

The features, advantages, and alternative aspects of the present invention will be apparent to those skilled in the art from a consideration of the following detailed description taken in combination with the accompanying drawings.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The term "analyte" as used herein means any molecule, molecules, material, substance, or matter that is to be analyzed or detected by Raman spectroscopy.

The term "Raman signal-enhancing material" as used herein means a material that, when formed into appropriate geometries or configurations, is capable of increasing the number of Raman-scattered photons that are scattered by an analyte when the analyte is located proximate to that material, and when the analyte and material are subjected to electromagnetic radiation. Raman signal-enhancing materials include, but are not limited to, silver, gold, and copper. Raman signal-enhancing materials generally are capable of exhibiting surface plasmon resonance when they are subjected to electromagnetic radiation at particular wavelengths. Raman signal-enhancing materials may be used to form Raman signal-enhancing structures.

The term "Raman signal-enhancing structure" as used herein means a structure that is capable of increasing the number of Raman-scattered photons that are scattered by an analyte when the analyte is located proximate to the structure, and the analyte and structure are subjected to electromagnetic radiation. Raman signal-enhancing structures include SERS-active structures and NERS-active structures.

The phrase "discontinuous layer of material" as used herein means any structure that can be formed by depositing a layer of material and subsequently removing at least a portion of the layer of material.

The illustrations presented herein are not meant to be actual views of any particular Raman device, Raman signal-enhancing structure, or Raman system, but are merely idealized representations which are employed to describe the present invention. Additionally, elements common between figures may retain the same numerical designation.

Figure 1:
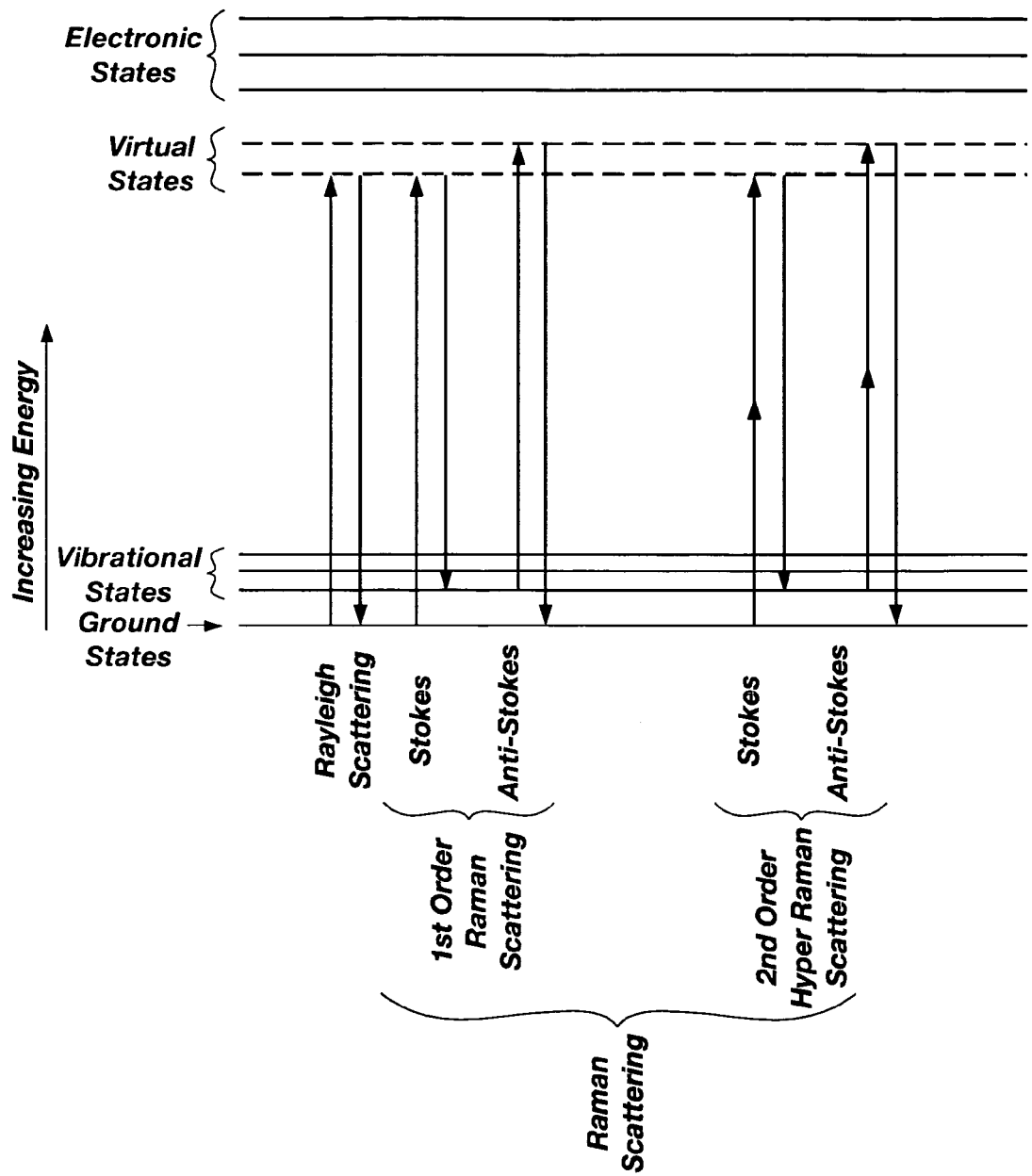
FIG. 1 is a Jablonski energy level diagram schematically representing Rayleigh and Raman scattering processes for a hypothetical analyte.
Figure 2A:
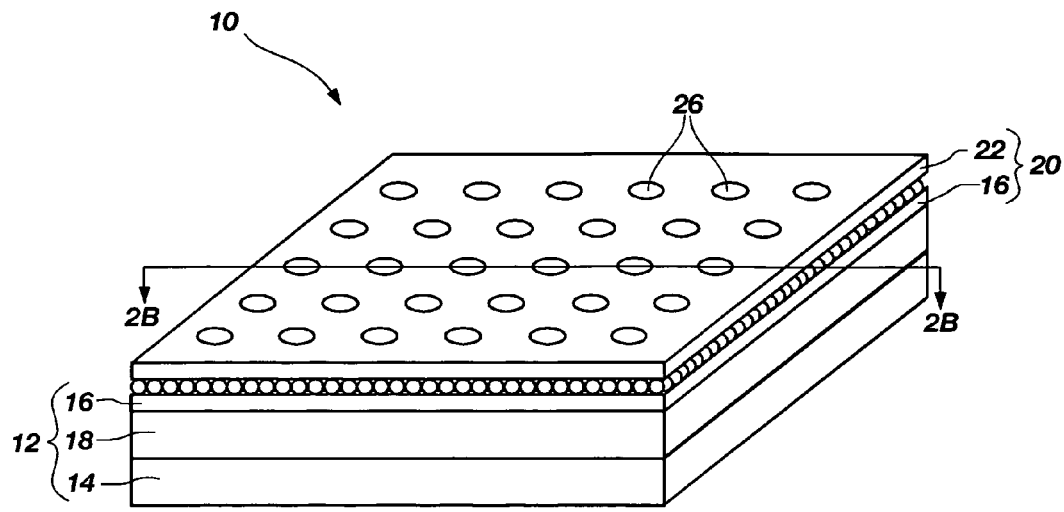
FIG. 2A is a perspective view of an embodiment of a Raman device of the present invention.
Figure 2B:
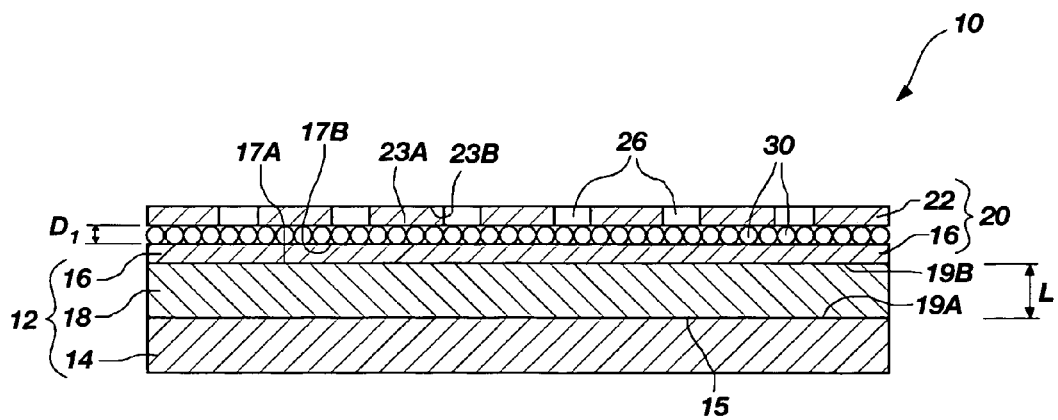
FIG. 2B is a cross-sectional view of the Raman device shown in FIG. 2A taken along section line 2B-2B shown therein.

A Raman device 10 that embodies teachings of the present invention is shown in FIGS. 2A-2B. The Raman device 10 includes a tunable resonant cavity 12 and a Raman signal-enhancing structure 20 coupled to the tunable resonant cavity 12. In this configuration, the Raman signal-enhancing structure 20 and an analyte 30 disposed proximate thereto may be irradiated by at least some electromagnetic radiation that is resonating within the resonant cavity 12. The tunable resonant cavity 12 may include a first reflective member 14, a second reflective member 16, and an electro-optic material 18 disposed between the first reflective member 14 and the second reflective member 16. Each of the first reflective member 14 and the second reflective member 16 may be electrically conductive and configured to apply a voltage across the electro-optic material. Furthermore, the second reflective member 16 may include a Raman signal-enhancing material.

By way of example and not limitation, the Raman signal-enhancing structure 20 that is coupled to the resonant cavity 12 may include the second reflective member 16 (which may include a Raman signal-enhancing material) and an additional layer of Raman signal-enhancing material 22. At least a portion of the additional layer of Raman signal-enhancing material 22 may be separated from the second reflective member 16 by a distance of less than about fifty (50) nanometers. In this configuration, the second reflective member 16 is part of both the resonant cavity 12 and the Raman signal-enhancing structure 20.

The electro-optic material 18 is capable of exhibiting a refractive index that varies in the presence of an applied electrical field. The electro-optic material 18 may include a substantially planar layer of electro-optic material 18 disposed between the first reflective member 14 and the second reflective member 16. In some embodiments, the electro-optic material 18 may include, but is not limited to, a crystalline material that is noncentrosymmetric (i.e., an atom with a position vector R from a point does not appear at –R). By way of example and not limitation, the electro-optic material 18 may include, but is not limited to, crystalline GaAs, $KH_2PO_4$ (potassium dihydrogen phosphate (KDP)), or $LiNbO_3$.

Each of the first reflective member 14 and the second reflective member 16 may be electrically conductive. In this configuration, the first reflective member 14 and the second reflective member 16 may provide a means for applying an external electrical field to the electro-optic material 18. For example, a voltage may be applied across the electro-optic material 18 between the first reflective member 14 and the second reflective member 16 to apply an external electrical field and vary the refractive index of the electro-optic material 18.

In alternative embodiments, the Raman device 10 may include at least two electrodes separate from the first reflective member 14 and the second reflective member 16 that are configured to apply a voltage across the electro-optic material 18 and to vary the refractive index of the electro-optic material 18. In such a configuration, the first reflective member 14 and the second reflective member 16 need not be electrically conductive.

Referring to FIG. 2B, the substantially planar layer of electro-optic material 18 may have a substantially planar first major surface 19A and a substantially planar second major surface 19B. The first reflective member 14 and the second reflective member 16 each may include a substantially planar layer of reflective material. The first reflective member 514 may be disposed on the first major surface 19A of the layer of electro-optic material 18, and the second reflective member 16 may be disposed on the second major surface 19B of the layer of electro-optic material 18. The second reflective member 16 may have a substantially planar first major surface 17A and a substantially planar second major surface 17B. Similarly, the additional layer of Raman signal-enhancing material 22 may be substantially planar and may have a substantially planar first major surface 23A and a substantially planar second major surface 23B.

The additional layer of Raman signal-enhancing material 22 may be oriented substantially parallel relative to the second reflective member 16, and the first major surface 23A of the additional layer of Raman signal-enhancing material 22 may be separated from the second major surface 17B of the second reflective member 16 by a distance $D_1$. The distance $D_1$ may be in a range from about one (1) nanometer to about fifty (50) nanometers. More particularly, the distance $D_1$ may be in a range from about one (1) nanometer to about twenty (20) nanometers.

The first reflective member 14 and the second reflective member 16 each may have a reflectivity that is greater than zero with respect to electromagnetic radiation having wavelengths in a range extending from about one-hundred (100) nanometers to about five-thousand (5,000) nanometers. By way of example and not limitation, the first reflective member 14 and the second reflective member 16 each may include a substantially planar layer of silver, copper, or gold. The first reflective member 14 may have a thickness greater than a thickness of the second reflective member 16. The first reflective member 14 may have a reflectivity of close to one-hundred (100) percent with respect to electromagnetic radiation having wavelengths in a range extending from about one-hundred (100) nanometers to about five-thousand (5,000) nanometers. The second reflective member 16 may be sufficiently thin to exhibit a reflectivity in a range from about twenty (20) percent to about eighty (80) percent with respect to electromagnetic radiation having wavelengths in a range extending from about one-hundred (100) nanometers to about five-thousand (5,000) nanometers.

The additional layer of Raman signal-enhancing material 22 may be sufficiently thin to allow as much electromagnetic radiation as possible to pass through the additional layer of Raman signal-enhancing material 22. By way of example and not limitation, the additional layer of Raman signal-enhancing material 22 may have a reflectivity of less than about fifty (50) percent with respect to electromagnetic radiation having wavelengths in a range extending from about one-hundred (100) nanometers to about five-thousand (5,000) nanometers.

By way of example and not limitation, a plurality of apertures 26 may be provided in the additional layer of Raman signal-enhancing material 22 to provide surface plasmon-enhanced transmission of electromagnetic radiation through the additional layer of Raman signal-enhancing material 22. Each aperture 26 may extend through the additional layer of Raman signal-enhancing material 22 from the first major surface 23A to the second major surface 23B. By way of example and not limitation, each aperture 26 of the plurality of apertures 26 may have a shape that is substantially cylindrical having a diameter between about twenty (20) nanometers and about one-thousand (1,000) nanometers. Furthermore, the plurality of apertures 26 may be disposed in an ordered array in the additional layer of Raman signal-enhancing material 22. For example, the plurality of apertures 26 may be disposed in a square lattice in the additional layer of Raman signal-enhancing material 22. The square lattice may have a periodicity (i.e., the distance between the centers of adjacent apertures 26 in the square lattice) of between about thirty (30) nanometers and about three-thousand (3,000) nanometers. In this configuration, electromagnetic radiation that is incident on the second major surface 23B of the additional layer of Raman signal-enhancing material 22 may excite surface plasmon waves on the second major surface 23B. These surface plasmon waves may be resonantly coupled through the apertures 26 to the first major surface 23A of the additional layer of Raman signal-enhancing material 22. The surface plasmon waves on the first major surface 23A may be converted back into electromagnetic radiation. In this manner, the apertures 26 may enable surface plasmon-enhanced transmission of electromagnetic radiation through the additional layer of Raman signal-enhancing material 22.

The tunable resonant cavity 12 may behave as a tunable Fabry-Perot resonant cavity and may be configured to resonate wavelengths of electromagnetic radiation in a range from about one-hundred (100) nanometers to about five-thousand (5,000) nanometers. Electromagnetic radiation within the resonant cavity 12 may be reflected back and forth between the first reflective member 14 and the second reflective member 16 in a direction substantially perpendicular to a major surface 15 of the first reflective member 14 and the first major surface 17A of the second reflective member 16.

The effective length $L_{eff}$ of the resonant cavity 12 may be defined as the length L separating the major surface 15 of the first reflective member 14 and the first major surface 17A of the second reflective member 16 multiplied by the refractive index of the electro-optic material 18 (i.e., $L_{eff}=n_{ri}L$, where $n_{ri}$ is the refractive index of the electro-optic material 18 and L is the distance separating the major surface 15 of the first reflective member 14 and the first major surface 17A of the second reflective member 16). If the effective length $L_{eff}$ is not equal to an integer multiple of one-half of the wavelength of the reflecting electromagnetic radiation (i.e., $L_{eff} \neq n\lambda/2$, where n is an integer and A is the wavelength of the reflecting electromagnetic radiation), the rays of radiation reflecting back and forth between the first reflective member 14 and the second reflective member 16 may interfere destructively. If, however, the effective length $L_{eff}$ is equal to an integer multiple of one-half of the wavelength of the reflecting electromagnetic radiation (i.e., $L_{eff}=n\lambda/2$), the rays of radiation reflecting back and forth between the first reflective member 14 and the second reflective member 16 may interfere constructively, thereby increasing the intensity or power of the electromagnetic radiation within the tunable resonant cavity 12.

To conduct Raman spectroscopy on an analyte using the Raman device 10 shown in FIGS. 2A-2B, an analyte 30 may be provided proximate the second reflective member 16 and the additional layer of Raman signal-enhancing material 22. For example, an analyte 30 may be provided between the second reflective member 16 and the additional layer of Raman signal-enhancing material 22. The analyte 30 may comprise a plurality of molecules disposed between the second reflective member 16 and the additional layer of Raman signal-enhancing material 22. Furthermore, the plurality of molecules may be disposed in a monolayer of molecules. The monolayer of molecules may be a self-assembled monolayer of molecules.

The second major surface 23B of the additional layer of Raman signal-enhancing material 22 may be irradiated with monochromatic incident electromagnetic radiation (not shown) having a wavelength in a range extending from about one-hundred (100) nanometers to about five-thousand (5,000) nanometers. At least a portion of the incident electromagnetic radiation may pass through the additional layer of Raman signal-enhancing material 22 and the second reflective member 16 and into the tunable resonant cavity 12. The tunable resonant cavity 12 may be tuned to resonate the incident electromagnetic radiation by electrically coupling a voltage source (not shown) (such as, for example, a battery) to the first reflective member 14 and the second reflective member 16 and applying a voltage between the first reflective member 14 and the second reflective member 16 to apply an external electrical field to the electro-optic material 18. The magnitude of the voltage may be selectively varied until at least some of the incident electromagnetic radiation is resonating within the resonant cavity 12.

As the reflectivity of the second reflective member 16 is less than one-hundred percent, at least some of the resonating incident electromagnetic radiation may pass through the second reflective member 16 and impinge on or irradiate the analyte 30. At least some of the incident electromagnetic radiation impinging on the analyte 30 may be inelastically scattered by the analyte 30, thereby generating Raman-scattered radiation. The Raman-scattered radiation may be detected using an electromagnetic radiation detector (not shown) and used to identify, analyze, or otherwise characterize the analyte 30. At least some of the Raman-scattered radiation emitted from the analyte may exit the Raman device 10 through the additional layer of Raman signal-enhancing material 22 or from the lateral side of the Raman device 10 where it may be detected. The Raman signal emitted by the analyte 30 may be enhanced by providing the analyte 30 adjacent the Raman signal-enhancing structure 20 and irradiating the analyte 30 and the Raman signal-enhancing structure 20 with incident electromagnetic radiation. The Raman signal emitted by the analyte 30 may be further enhanced by coupling the Raman signal-enhancing structure 20 to the tunable resonant cavity 12 and irradiating the analyte 30 and the Raman signal-enhancing structure 20 with at least a portion of the incident electromagnetic radiation that is resonating within the tunable resonant cavity 12.

The Raman device 10 previously described herein includes a generally layered structure, which may be fabricated in a layer-by-layer sequence. Methods for forming the Raman device 10 shown in FIGS. 2A-2B are described below.

Referring to FIG. 2B, the first reflective member 14 may be provided in the form of a commercially available substrate comprising a Raman signal-enhancing material, such as, for example, silver, copper, or gold.

A substantially planar layer of electro-optic material 18 may be deposited over, or formed on, at least a portion of the first reflective member 16 using physical vapor deposition techniques (PVD), including but not limited to, thermal evaporation techniques, electron-beam evaporation techniques, filament evaporation techniques, and sputtering techniques. Alternatively, the substantially planar layer of electro-optic material 18 may be formed or grown on the first reflective member 16 using chemical vapor deposition techniques (CVD), including but not limited to, atomic layer deposition techniques.

After forming the substantially planar layer of electro-optic material 18, the second reflective member 16 may be formed on or over the layer of electro-optic material 18. The second reflective member 16 may be deposited over the layer of electro-optic material 18 using, for example, any of the previously described physical vapor deposition techniques (PVD).

After forming the second reflective member 16, a layer of molecules or other analyte 30 may be deposited over at least a portion of the second reflective member 16. The layer of molecules may be deposited using Langmuir film and Langmuir-Blodgett film techniques. These techniques generally include forming a monolayer of molecules on a surface of a liquid and passing the second reflective member 16 (together with the underlying layer of electro-optic material 18 and the first reflective member 14) through the layer of molecules to transfer the layer of molecules to the surface of the second reflective member 16. Equipment for depositing Langmuir films and Langmuir-Blodgett films is commercially available from, for example, KSV Instruments of Helsinki, Finland.

In alternative methods, the analyte 30 may be suspended in a liquid, and the suspension may be applied to the second major surface 17B of the second reflective member 16. The liquid then may be allowed to evaporate, leaving the analyte 30 on the second major surface 17B of the second reflective member 16. In yet other methods, the analyte 30 may be simply adsorbed on the second major surface 17B of the second reflective member 16.

Additionally, the analyte 30 may be bound to the second reflective member 16 or the additional layer of Raman signal-enhancing material 22 using an intermediate binding molecule or material (not shown). The binding material may include any molecule or material that will bind to the analyte 30. By way of example and not limitation, the analyte 30 may include a particular molecule, and the binding material may include a molecule that, together with the analyte 30, form what is known in the art as a "specific pair" or a "recognition pair" of molecules. For example, if the analyte 30 is an antigen or an antibody, the binding material may include a complementary antigen or antibody. Many biomolecules act as receptors or ligands to other biomolecules. If the analyte 30 is or includes such a biomolecule, the binding material may include a complementary biomolecule.

After the layer of molecules or other analyte 30 has been deposited over at least a portion of the second reflective member 16, the additional layer of Raman signal-enhancing material 22 may be deposited over at least a portion of the analyte 30. By way of example and not limitation, the additional layer of Raman signal-enhancing material 22 may be deposited over the analyte 30 using physical vapor deposition techniques (PVD) including, but not limited to, thermal evaporation techniques, electron-beam evaporation techniques, filament evaporation techniques, and sputtering techniques.

After depositing the additional layer of Raman signal-enhancing material 22 over the analyte 30, the apertures 26 may be formed in the additional layer of Raman signal-enhancing material 22. The apertures 26 may be formed using various methods including, for example, photolithography, electron beam lithography, or focused ion beam lithography.

Figure 3A:
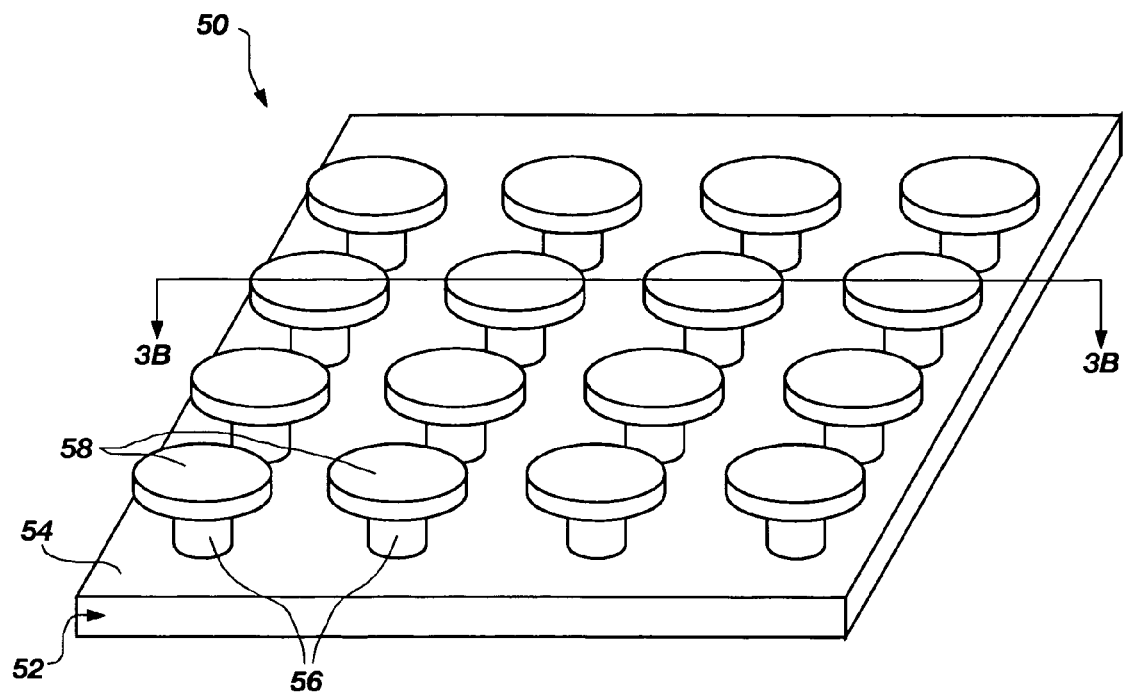
FIG. 3A is a perspective view of an embodiment of a Raman signal-enhancing structure of the present invention.

A Raman signal-enhancing structure 50 that embodies a particular embodiment of the present invention is shown in FIGS. 3A-3E. Referring to FIG. 3A, the Raman signal-enhancing structure 50 may include a layer of Raman signal-enhancing material 52 having a major surface 54, at least one support structure 56 extending from the major surface 54 of the layer of Raman signal-enhancing material 52, and at least one member 58 comprising a Raman signal-enhancing material disposed on an end of the at least one support structure 56 opposite the layer of Raman signal-enhancing material 52. Each of the layer of Raman signal-enhancing material 52 and the member 58 comprising a Raman signal-enhancing material may be substantially planar.

Figure 3B:
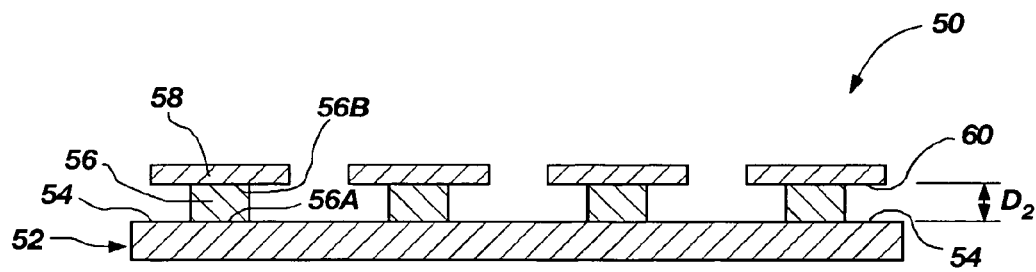
FIG. 3B is a cross-sectional view of the Raman signal-enhancing structure shown in FIG. 3A taken along section line 3B-3B shown therein.

Referring to FIG. 3B, the support structure 56 may separate at least a portion of the member 58 comprising a Raman signal-enhancing material from the layer of Raman signal-enhancing material 52 by a selected distance $D_2$ of less than about fifty (50) nanometers. More particularly, the selected distance $D_2$ may be less than about twenty (20) nanometers.

By way of example and not limitation, each support structure 56 may be substantially cylindrical having a length and a diameter. A first end 56A of each substantially cylindrical support structure 56 may be structurally secured to the major surface 54 of the layer of Raman signal-enhancing material 52. Furthermore, each member 58 comprising a Raman signal-enhancing material also may be substantially cylindrical having a length and a diameter. A second end 56B of each substantially cylindrical support structure 56 may be structurally secured to an end of a member 58. As seen in FIG. 3B, the diameter of each support structure 56 may be less than the diameter of each member 58 disposed thereon. In this configuration, at least a portion of each member 58 may extend laterally beyond a lateral surface of the underlying support structure 56 to define a gap between a surface of each member 58 (such as an end 60 of each member 58) and the major surface 54 of the layer of Raman signal-enhancing material 52.

In one embodiment of the invention, the Raman signal-enhancing structure 50 may include a plurality of planar members 58. Each planar member of the plurality may comprise a Raman signal-enhancing material. Furthermore, each planar member 58 may be disposed on an end of a support structure 56. Furthermore, the plurality of planar members 58 may be disposed in an ordered array over the major surface 54 of the layer of Raman signal-enhancing material 52. Each planar member 58 may have a diameter in a range from about ten (10) nanometers to about one-hundred (100) nanometers, and each support structure 56 may have a diameter that is between about fifty (50) percent and about eighty (80) percent of the diameter of each planar member 58. The distance separating the centers of adjacent planar members 58 may be between about twenty (20) nanometers and about three-hundred (300) nanometers.

Figure 3C:
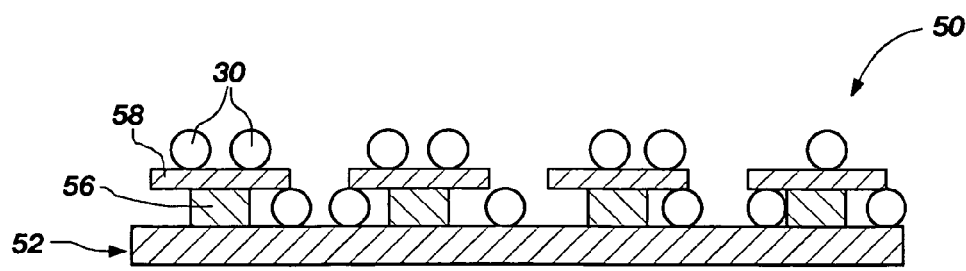
FIG. 3C is a cross-sectional view of the Raman signal-enhancing structure shown in FIG. 3A like that shown in FIG. 3B further illustrating analyte molecules disposed on the Raman signal-enhancing structure.

To conduct Raman spectroscopy on an analyte using the Raman signal-enhancing structure 50, an analyte 30 may be provided on the surfaces of the Raman signal-enhancing structure 50, as shown in FIG. 3C. By way of example and not limitation, the analyte 30 may comprise one or more molecules. Furthermore, the molecules may be disposed at various locations on the Raman signal-enhancing structure 50, including the gaps between each member 58 comprising a Raman signal-enhancing material and the layer of Raman signal-enhancing material 52. The Raman signal emitted by the analyte 30 may be enhanced by providing the analyte 30 adjacent the Raman signal-enhancing structure 50 and irradiating the analyte 30 and the Raman signal-enhancing structure 50 with incident electromagnetic radiation.

The degree of enhancement provided by the Raman signal-enhancing structure 50 to the Raman signal emitted by the analyte 30 may be at least partially dependent on the distance $D_2$ separating each member 58 comprising a Raman signal-enhancing material from the layer of Raman signal-enhancing material 52. Furthermore, the particular distance $D_2$ that provides optimal enhancement of the Raman signal may be at least partially dependent on the particular analyte 30. Therefore, the distance $D_2$ may be selected to optimize the enhancement to the Raman signal emitted by the particular analyte 30 being analyzed.

In one embodiment of the invention, each support structure 56 may include a material that is configured to elastically deform when a voltage is applied between the layer of Raman signal-enhancing material 52 and the member 58 adjacent the support structure 56. By way of example and not limitation, each support structure 56 may include a piezoelectric material, such as, for example, quartz (substantially crystalline $SiO_2$), barium titanate ($BaTiO_3$), lead zirconate titanate ($PbTi_{1-x}ZrxO_3$) (often referred to as "PZT"), or amorphous silicon (α-Si).

Figure 3D:
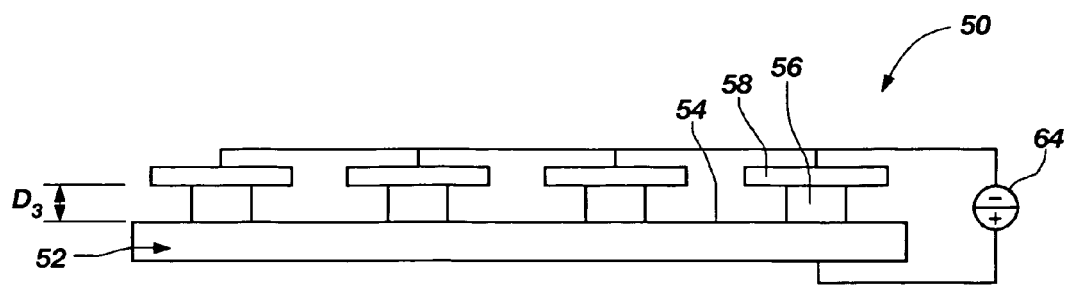
FIG. 3D is a side view of the Raman signal-enhancing structure shown in FIG. 3A.

Referring to FIG. 3D, a voltage source 64 may be provided and electrically coupled to the layer of Raman signal-enhancing material 52 and the members 58 comprising a Raman signal-enhancing material. The crystal structure of the piezoelectric material may be oriented such that each support structure 56 will extend in a direction substantially normal to the major surface 54 of the layer of Raman signal-enhancing material 52 when a voltage having a first polarity is applied between the layer of Raman signal-enhancing material 52 and the members 58 comprising a Raman signal-enhancing material. Extending each support structure 56 in such a direction may provide a distance $D_3$ between the major surface 54 of the layer of Raman signal-enhancing material 52 and each member 58 that is larger than the distance $D_2$ shown in FIG. 3B.

Figure 3E:
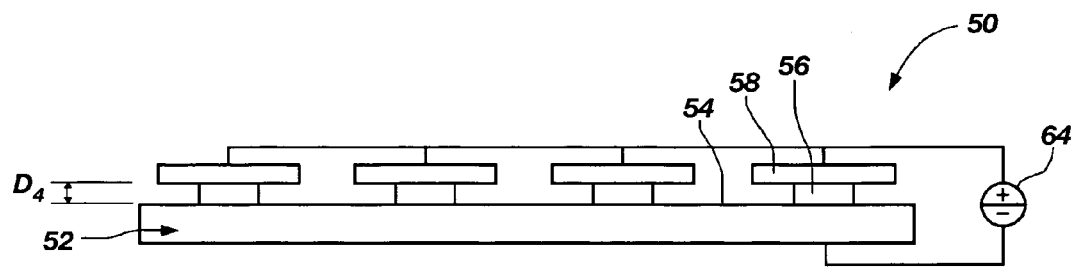
FIG. 3E is a side view of the Raman signal-enhancing structure shown in FIG. 3A like that shown in FIG. 3D further illustrating a voltage source applying a voltage between elements of the Raman signal-enhancing structure.

Referring to FIG. 3E, reversing the polarity of the voltage applied between the layer of Raman signal-enhancing material 52 and the members 58 comprising a Raman signal-enhancing material may cause each support structure 56 to contract in a direction substantially normal to the major surface 54 of the layer of Raman signal-enhancing material 52. Contracting each support structure 56 in such a direction may provide a distance $D_4$ between the major surface 54 of the layer of Raman signal-enhancing material 52 and each member 58 that is smaller than the distance $D_2$ shown in FIG. 3B.

In such a configuration, an analyte 30 (FIG. 3C) may be provided adjacent the Raman signal-enhancing structure 50, and the analyte 30 and the Raman signal-enhancing structure 50 may be irradiated with incident electromagnetic radiation (not shown) while varying the polarity and the magnitude of the voltage between the layer of Raman signal-enhancing material 52 and the members 58 until the Raman signal emitted by the particular analyte 30 is optimally enhanced.

In alternative embodiments of the present invention, an external electrical field may be applied to the piezoelectric material of the support structures 56 by methods other than applying a voltage between the layer of Raman signal-enhancing material 52 and the members 58. Any method of generating an electrical field in a region containing the support structures 56 may be used to vary the distance between the layer of Raman signal-enhancing material 52 and the members 58.

Figure 4:
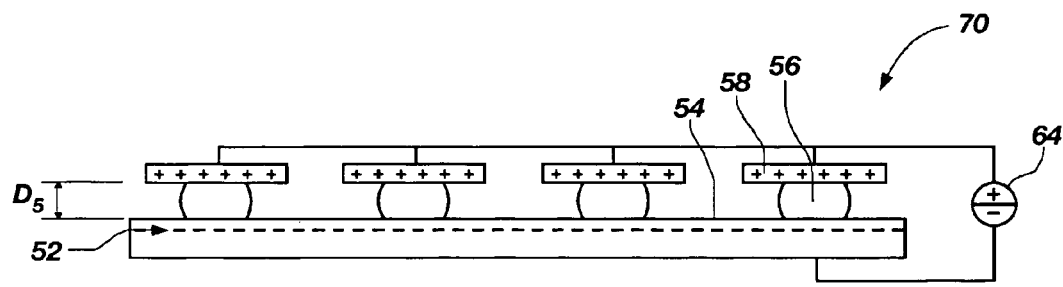
FIG. 4 is a side view of another embodiment of a Raman signal-enhancing structure of the present invention.

Another Raman signal-enhancing structure 70 that embodies teachings of the present invention is shown in FIG. 4. As seen therein, the Raman signal-enhancing structure 70 is substantially similar to the Raman signal-enhancing structure 50 shown in FIGS. 3A-3E and includes a layer of Raman signal-enhancing material 52 having a major surface 54, at least one support structure 56 extending from the major surface 54 of the layer of Raman signal-enhancing material 52, and at least one member 58 comprising a Raman signal-enhancing material disposed on an end of the at least one support structure 56 opposite the layer of Raman signal-enhancing material 52. In the Raman signal-enhancing structure 70 shown in FIG. 4, however, each support structure 56 may include an elastic material that is electrically insulating and capable of elastically deforming in response to electrostatic forces generated when a voltage is applied between the layer of Raman signal-enhancing material 52 and the member 58 adjacent the support structure 56.

As seen in FIG. 4, when a voltage difference is applied between the layer of Raman signal-enhancing material 52 and the members 58 comprising a Raman signal-enhancing material, opposite electrical charges may accumulate on the layer of Raman signal-enhancing material 52 and the members 58. When the charges are opposite, as illustrated in FIG. 4, an attractive electrostatic force may be applied between the layer of Raman signal-enhancing material 52 and the members 58, which may cause each support structure 56 to contract in a direction substantially normal to the major surface 54 of the layer of Raman signal-enhancing material 52. Contracting each support structure 56 in such a direction may provide a distance $D_5$ between the major surface 54 of the layer of Raman signal-enhancing material 52 and each member 58 that is smaller than the distance in the absence of an applied voltage. Furthermore, when the charges are similar, a repulsive electrostatic force may be applied between the layer of Raman signal-enhancing material 52 and the members 58, which may cause each support structure 56 to extend in a direction substantially normal to the major surface 54 of the layer of Raman signal-enhancing material 52. As a result, an analyte 30 (FIG. 3C) may be provided adjacent the Raman signal-enhancing structure 70, and the analyte 30 and the Raman signal-enhancing structure 70 may be irradiated with incident electromagnetic radiation (not shown) while varying the polarity and the magnitude of the voltage between the layer of Raman signal-enhancing material 52 and the members 58 until the Raman signal emitted by the analyte 30 is optimally enhanced.

Figure 5:
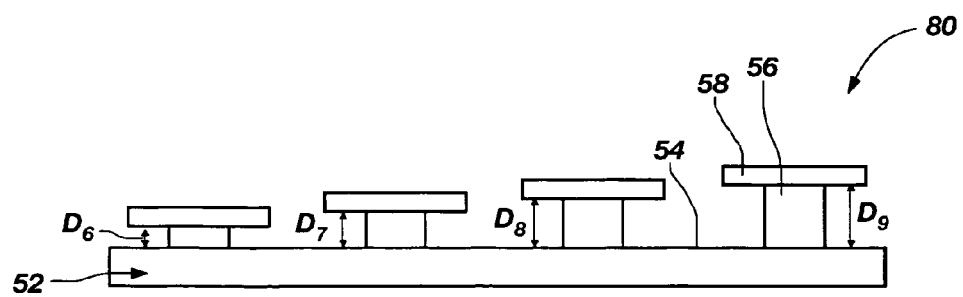
FIG. 5 is a side view of yet another embodiment of a Raman signal-enhancing structure of the present invention.

Yet another Raman signal-enhancing structure 80 that embodies teachings of the present invention is shown in FIG. 5. As seen therein, the Raman signal-enhancing structure 80 is substantially similar to the Raman signal-enhancing structure 50 shown in FIGS. 3A-3E and includes a layer of Raman signal-enhancing material 52 having a major surface 54, a plurality of support structures 56 extending from the major surface 54 of the layer of Raman signal-enhancing material 52, and a plurality of members 58 comprising a Raman signal-enhancing material disposed on the ends of the support structures 56 opposite the layer of Raman signal-enhancing material 52. In the Raman signal-enhancing structure shown in FIG. 5, however, the plurality of support structures 56 includes support structures 56 that extend from the major surface 54 of the layer of Raman signal-enhancing material 52 by a variety of distances, thereby providing a variety of distances between the members 58 comprising a Raman signal-enhancing material and the layer of Raman signal-enhancing material 52.

By way of example and not limitation, at least one support structure 56 may separate at least a portion of the member 58 comprising a Raman signal-enhancing material from the layer of Raman signal-enhancing material 52 by a selected distance $D_6$, at least one support structure 56 may separate at least a portion of the member 58 comprising a Raman signal-enhancing material from the layer of Raman signal-enhancing material by a selected distance $D_7$, at least one support structure 56 may separate at least a portion of the member 58 comprising a Raman signal-enhancing material from the layer of Raman signal-enhancing material by a selected distance $D_8$, and at least one support structure 56 may separate at least a portion of the member 58 comprising a Raman signal-enhancing material from the layer of Raman signal-enhancing material by a selected distance $D_9$. Each of the distances $D_6$, $D_7$, $D_8$, and $D_9$ may be less than about fifty (50) nanometers. More particularly, each of the distances $D_6$, $D_7$, $D_8$, and $D_9$ may be less than about twenty (20) nanometers. In this configuration, an analyte 30 (FIG. 3C) may be provided adjacent the Raman signal-enhancing structure 80, and the analyte 30 and the Raman signal-enhancing structure 80 may be irradiated with incident electromagnetic radiation (not shown).

As previously discussed, the degree of enhancement to the Raman signal emitted by the analyte 30 that is provided by the Raman signal-enhancing structure 80 may be at least partially dependent on the distance separating each member 58 comprising a Raman signal-enhancing material from the layer of Raman signal-enhancing material 52. Furthermore, the particular distance that provides optimal enhancement of the Raman signal may be at least partially dependent on the particular analyte 30. By providing a variety of distances separating the members 58 comprising a Raman signal-enhancing material from the layer of Raman signal-enhancing material 52, at least one of the distances may optimally enhance the Raman signal emitted by a particular analyte 30 being analyzed using the Raman signal-enhancing structure 80.

Figure 6A:
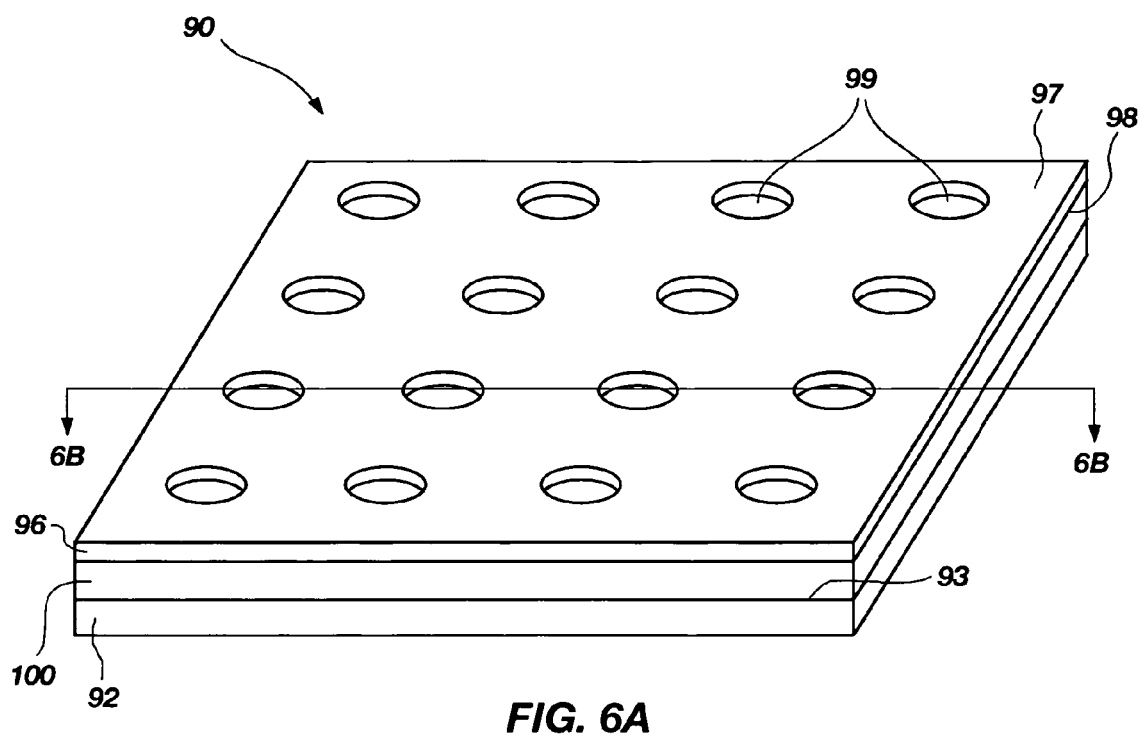
FIG. 6A is a perspective view of another embodiment of a Raman signal-enhancing structure of the present invention.

Another Raman signal-enhancing structure 90 that embodies teachings of the present invention is shown in FIGS. 6A-6D. Referring to FIG. 6A, the Raman signal-enhancing structure 90 may include a first layer of Raman signal-enhancing material 92, a second layer of Raman signal-enhancing material 96, and a discontinuous layer of support material 100 disposed between the first layer of Raman signal-enhancing material 92 and the second layer of Raman signal-enhancing material 96. The discontinuous layer of support material 100 may be disposed on and extend from a major surface 93 of the first layer of Raman signal-enhancing material 92. The first layer of Raman signal-enhancing material 92 and the second layer of Raman signal-enhancing material 96 each may be substantially planar.

The second layer of Raman signal-enhancing material 96 may include a first major surface 97 and a second major surface 98. The second layer of Raman signal-enhancing material 96 may also include a plurality of apertures 99 extending through the second layer of Raman signal-enhancing material 96 from the first major surface 97 to the second major surface 98. In one embodiment, each aperture 99 may have a shape that is substantially cylindrical having a diameter that is less than about 50 nanometers. Furthermore, the plurality of apertures 99 may be disposed in an ordered array in the second layer of Raman signal-enhancing material 96. The plurality of apertures 99 may be configured to enable surface plasmon-enhanced transmission of electromagnetic radiation through the second layer of Raman signal-enhancing material 96.

Figure 6B:
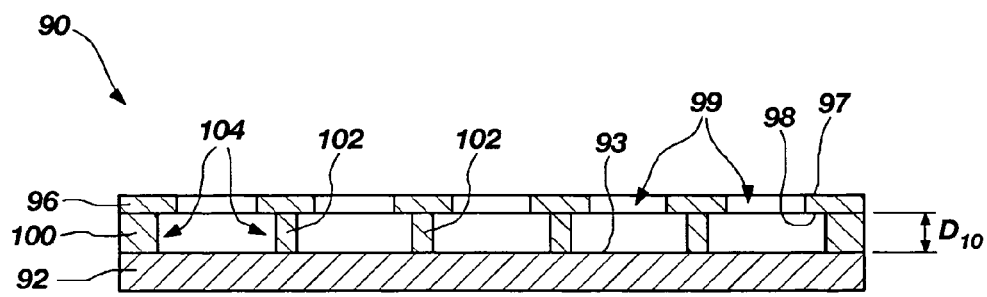
FIG. 6B is a cross-sectional view of the Raman signal-enhancing structure shown in FIG. 6A taken along section line 6B-6B shown therein.

Referring to FIG. 6B, the discontinuous layer of support material 100 may separate at least a portion of the second layer of Raman signal-enhancing material 96 from the first layer of Raman signal-enhancing material 92 by a selected distance $D_{10}$ of less than about fifty (50) nanometers. More particularly, the selected distance $D_{10}$ may be less than about twenty (20) nanometers.

By way of example and not limitation, the discontinuous layer of support material 100 may include a plurality of isolated regions of support material 102. Each isolated region of support material 102 may have a shape that is substantially cylindrical having a diameter that is less than about fifty (50) nanometers. Furthermore, each isolated region of support material 102 may be disposed between the first layer of Raman signal-enhancing material 92 and the second layer of Raman signal-enhancing material 96 at a lateral location between the apertures 99 extending through the second layer of Raman signal-enhancing material 96. In this configuration, an analyte 30 may be provided access to regions 104 that are located between the first layer of Raman signal-enhancing material 92 and the second layer of Raman signal-enhancing material 96 through the apertures 99.

Figure 6C:
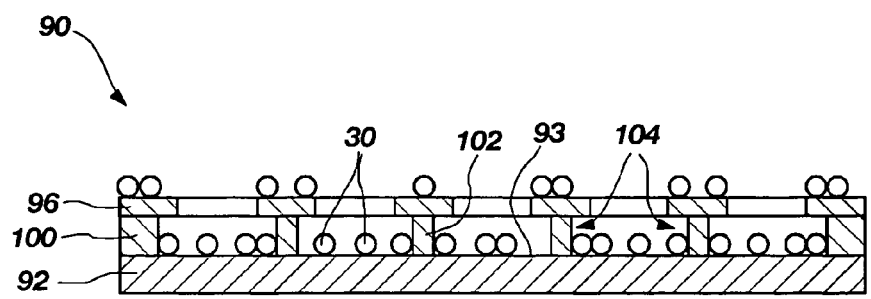
FIG. 6C is a cross-sectional view of the Raman signal-enhancing structure shown in FIG. 6A like that shown in FIG. 6B further illustrating analyte molecules disposed on the Raman signal-enhancing structure.

To conduct Raman spectroscopy on an analyte using the Raman signal-enhancing structure 90 shown in FIG. 6A, an analyte 30 may be provided on the surfaces of the Raman signal-enhancing structure 90, as shown in FIG. 6C. By way of example and not limitation, the analyte 30 may comprise one or more molecules. Furthermore, the molecules may be disposed at various locations on the Raman signal-enhancing structure 90 including the regions 104 that are located between the first layer of Raman signal-enhancing material 92 and at least a portion of the second layer of Raman signal-enhancing material 96. The Raman signal emitted by the analyte 30 may be enhanced by providing the analyte 30 adjacent the Raman signal-enhancing structure 90 and irradiating the analyte 30 and the Raman signal-enhancing structure 90 with incident electromagnetic radiation.

The degree of enhancement provided to the Raman signal emitted by the analyte 30 by the Raman signal-enhancing structure 90 may be at least partially dependent on the distance $D_{10}$ separating the second layer of Raman signal-enhancing material 96 from the first layer of Raman signal-enhancing material 92. Furthermore, the particular distance $D_{10}$ that provides optimal enhancement of the Raman signal may be at least partially dependent on the particular analyte 30. Therefore, the distance $D_{10}$ may be selected to optimally enhance the Raman signal emitted by the analyte 30.

In one embodiment of the invention, the discontinuous layer of support material 100 may include a material that is configured to elastically deform when a voltage is applied between the first layer of Raman signal-enhancing material 92 and the second layer of Raman signal-enhancing material 96. By way of example and not limitation, the discontinuous layer of support material 100 may include a piezoelectric material. For example, the discontinuous layer of support material 100 may include quartz (substantially crystalline $SiO_2$), barium titanate ($BaTiO_3$), lead zirconate titanate ($PbTi_{1-x}ZrxO_3$) (often referred to as "PZT"), or amorphous silicon ($\alpha$-Si).

Figure 6D:
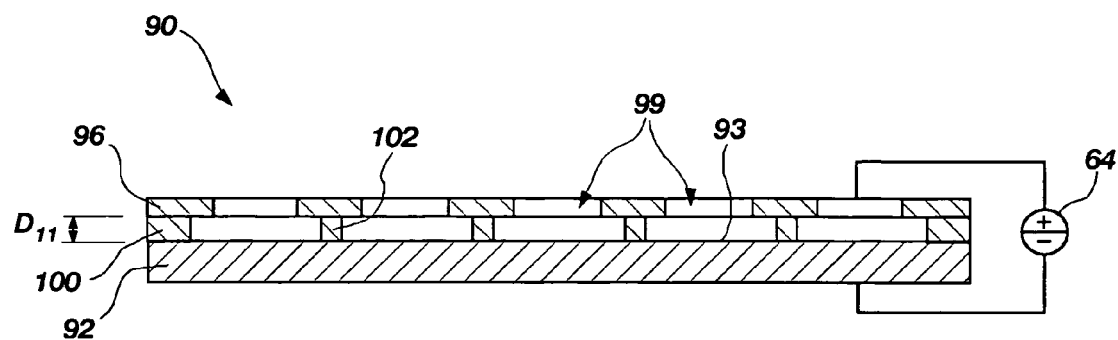
FIG. 6D is a side view of the Raman signal-enhancing structure shown in FIG. 6A like that shown in FIG. 6B further illustrating a voltage source applying a voltage between elements of the Raman signal-enhancing structure.

Referring to FIG. 6D, a voltage source 64 may be provided and electrically coupled to the first layer of Raman signal-enhancing material 92 and the second layer of Raman signal-enhancing material 96. The crystal structure of the piezoelectric material may be oriented such that each isolated region of support material 102 will contract in a direction substantially normal to the major surfaces 97, 98 of the second layer of Raman signal-enhancing material 96 when a voltage having a first polarity is applied between the first layer of Raman signal-enhancing material 92 and the second layer of Raman signal-enhancing material 96. Contracting each isolated region of support material 102 in such a direction may provide a distance $D_{11}$ between the first layer of Raman signal-enhancing material 92 and the second layer of Raman signal-enhancing material 96 that is less than the distance $D_{10}$ shown in FIG. 6B.

Reversing the polarity of the voltage applied between the first layer of Raman signal-enhancing material 92 and the second layer of Raman signal-enhancing material 96 may cause each isolated region of support material 102 to extend in a direction substantially normal to the major surfaces 97, 98 of the second layer of Raman signal-enhancing material 96. Extending each isolated region of support material 102 in such a direction may provide a distance (not shown) between the first layer of Raman signal-enhancing material 92 and the second layer of Raman signal-enhancing material 96 that is greater than the distance $D_{10}$ shown in FIG. 6B.

In such a configuration, an analyte 30 (FIG. 6C) may be provided adjacent the Raman signal-enhancing structure 90, and the analyte 30 and the Raman signal-enhancing structure 90 may be irradiated with incident electromagnetic radiation (not shown) while varying the polarity and the magnitude of the voltage between the first layer of Raman signal-enhancing material 92 and the second layer of Raman signal-enhancing material 96 until the Raman signal emitted by the analyte 30 is optimally enhanced.

In alternative embodiments of the present invention, an external electrical field may be applied to the piezoelectric material of the isolated regions of support material 102 by methods other than applying a voltage between the first layer of Raman signal-enhancing material 92 and the second layer of Raman signal-enhancing material 96. Any method of generating an electrical field in a region containing the isolated regions of support material 102 may be used to vary the distance between the first layer of Raman signal-enhancing material 92 and the second layer of Raman signal-enhancing material 96.

Figure 7:
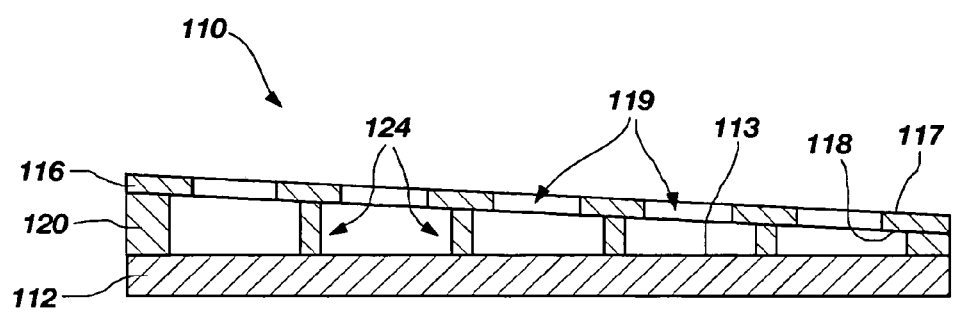
FIG. 7 is a cross-sectional side view of yet another embodiment of a Raman signal-enhancing structure of the present invention.

Yet another embodiment of a Raman signal-enhancing structure 110 of the present invention is shown in FIG. 7. As seen therein, the Raman signal-enhancing structure 110 is substantially similar to the Raman signal-enhancing structure 90 shown in FIGS. 6A-6D and includes a first layer of Raman signal-enhancing material 112, a second layer of Raman signal-enhancing material 116, and a discontinuous layer of support material 120 disposed between the first layer of Raman signal-enhancing material 112 and the second layer of Raman signal-enhancing material 116. Each of the first layer of Raman signal-enhancing material 112 and the second layer of Raman signal-enhancing material 116 may be substantially planar. The discontinuous layer of support material 120 may be disposed on and extend from a major surface 113 of the first layer of Raman signal-enhancing material 112. In the Raman signal-enhancing structure 110 shown in FIG. 7, however, a thickness of the discontinuous layer of support material 120 is varied in at least one direction across the Raman signal-enhancing structure 110 such that the first layer of Raman signal-enhancing material 112 is oriented at an angle with respect to the second layer of Raman signal-enhancing material 116. In this configuration, a variety of distances are provided between the first layer of Raman signal-enhancing material 112 and the second layer of Raman signal-enhancing material 116.

The second layer of Raman signal-enhancing material 116 may include a first major surface 117 and a second major surface 118. A plurality of apertures 119 may extend through the second layer of Raman signal-enhancing material 116 from the first major surface 117 to the second major surface 118. In one embodiment, each aperture 119 may have a shape that is substantially cylindrical having a diameter that is less than about fifty (50) nanometers. Furthermore, the plurality of apertures 119 may be disposed in an ordered array in the second layer of Raman signal-enhancing material 116. The plurality of apertures 119 may be configured to enable surface plasmon-enhanced transmission of electromagnetic radiation through the second layer of Raman signal-enhancing material 116.

By way of example and not limitation, the discontinuous layer of support material 120 may include a plurality of isolated regions of support material 122. Each isolated region of support material 122 may have a shape that is substantially cylindrical having a diameter that is less than about fifty (50) nanometers. Furthermore, each isolated region of support material 122 may be disposed between the first layer of Raman signal-enhancing material 112 and the second layer of Raman signal-enhancing material 116 at a location laterally between the apertures 119 extending through the second layer of Raman signal-enhancing material 116. In this configuration, access may be provided through the apertures 119 to regions 124 that are located between the first layer of Raman signal-enhancing material 112 and at least a portion of the second layer of Raman signal-enhancing material 116.

In this configuration, a plurality of distances may be provided between the first layer of Raman signal-enhancing material 112 and the second layer of Raman signal-enhancing material 116. The maximum distance between the first layer of Raman signal-enhancing material 112 and the second layer of Raman signal-enhancing material 116 may be less than about fifty (50) nanometers. More particularly, the maximum distance between the first layer of Raman signal-enhancing material 112 and the second layer of Raman signal-enhancing material 116 may be less than about twenty (20) nanometers. In this configuration, an analyte 30 (FIG. 6C) may be provided adjacent the Raman signal-enhancing structure 110, and the analyte 30 and the Raman signal-enhancing structure 110 may be irradiated with incident electromagnetic radiation (not shown).

As previously discussed, the degree to which the Raman signal-enhancing structure 110 enhances the Raman signal emitted by the analyte 30 may be at least partially dependent on the distance between the first layer of Raman signal-enhancing material 112 and the second layer of Raman signal-enhancing material 116. Furthermore, the particular distance that provides optimal enhancement of the Raman signal may be at least partially dependent on the particular analyte 30. By providing a variety of distances between the first layer of Raman signal-enhancing material 112 and the second layer of Raman signal-enhancing material 116, at least one of the distances may optimally enhance the Raman signal emitted by a particular analyte 30 being analyzed using the Raman signal-enhancing structure 110.

Raman signal-enhancing structures that embody teachings of the present invention, such as, for example, any one of the previously described Raman signal-enhancing structures 50, 70, 80, 90, and 110, may be provided adjacent to and coupled with a tunable resonant cavity, such as, for example, the previously described tunable resonant cavity 12 shown in FIGS. 2A-2B, to provide additional Raman devices that embody teachings of the present invention. For example, each of the Raman signal-enhancing structures 50, 70, 80, 90, and 110 includes a substantially planar layer of Raman signal enhancing material (52, 92, 112), which may be replaced by the second reflective member 16 of the tunable resonant cavity 12 shown in FIGS. 2A-2B.

Figure 8A:
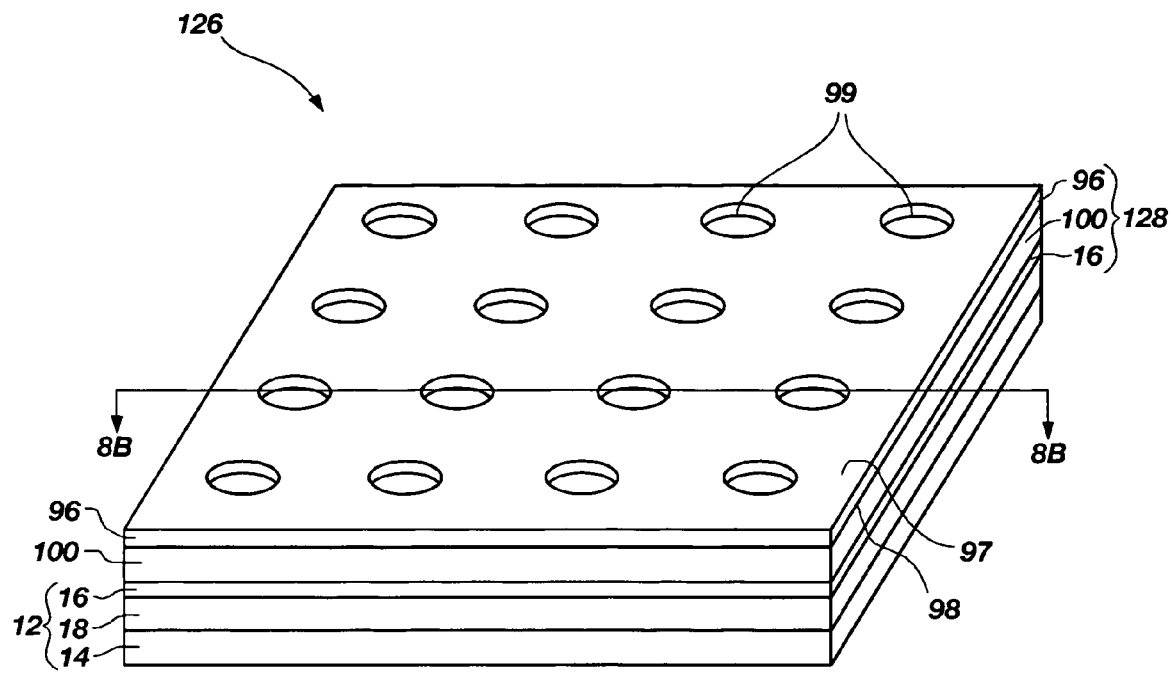
FIG. 8A is a perspective view of another embodiment of a Raman device of the present invention.
Figure 8B:
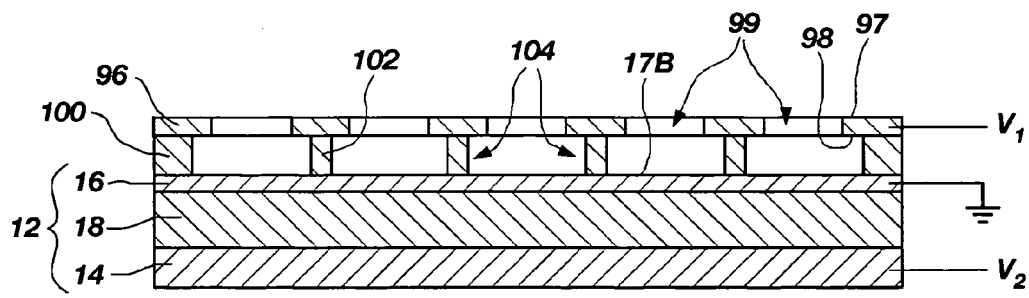
FIG. 8B is a cross-sectional view of the Raman device shown in FIG. 8A taken along section line 8B-8B shown therein.

Another Raman device 126 that embodies teachings of the present invention is shown in FIGS. 8A-8B. Referring to FIG. 8A, the Raman device 126 includes a tunable resonant cavity 12 as previously described in relation to FIGS. 2A-2B, and a Raman signal-enhancing structure 128 coupled to the tunable resonant cavity 12. The Raman signal-enhancing structure 128 is substantially similar to the previously described Raman signal-enhancing structure 90 shown in FIGS. 6A-6D; however, the layer of Raman signal enhancing material 92 (FIG. 6A) has been replaced by the second reflective member 16 of the tunable resonant cavity 12. As previously described, the tunable resonant cavity 12 may include a first reflective member 14, a second reflective member 16, and an electro-optic material 18 disposed between the first reflective member 14 and the second reflective member 16. Each of the first reflective member 14 and the second reflective member 16 may be electrically conductive and configured to apply a voltage across the electro-optic material to change the refractive index of the electro-optic material. Furthermore, the second reflective member 16 may include a Raman signal-enhancing material.

By way of example and not limitation, the Raman signal-enhancing structure 128 that is coupled to the resonant cavity 12 may include the second reflective member 16 (which may include a Raman signal-enhancing material), a second layer of Raman signal-enhancing material 96, and a discontinuous layer of support material 100 disposed between the second reflective member 16 and the second layer of Raman signal-enhancing material 96. In this configuration, the second reflective member 16 is part of both the resonant cavity 12 and the Raman signal-enhancing structure 128.

The second layer of Raman signal-enhancing material 96 may include a first major surface 97 and a second major surface 98. A plurality of apertures 99 may extend through the second layer of Raman signal-enhancing material 96 from the first major surface 97 to the second major surface 98.

Referring to FIG. 8B, the discontinuous layer of support material 100 may separate at least a portion of the second layer of Raman signal-enhancing material 96 from the first layer of Raman signal-enhancing material 92 by a selected distance of less than about fifty (50) nanometers. More particularly, the selected distance may be less than about twenty (20) nanometers.

As previously discussed, the discontinuous layer of support material 100 may include a plurality of isolated regions of support material 102. In this configuration, an analyte may be provided access to regions 104 that are located between the first layer of Raman signal-enhancing material 92 and the second layer of Raman signal-enhancing material 96 through the apertures 99.

To conduct Raman spectroscopy on an analyte using the Raman device 128 shown in FIGS. 8A-8B, an analyte (not shown) may be provided between the second reflective member 16 and the second layer of Raman signal-enhancing material 96.

In one embodiment, the second reflective member 16 may be grounded, a first voltage $V_1$ may be applied to the second layer of Raman signal-enhancing material 96, and a second voltage $V_2$ may be applied to the first reflective member 14.

The Raman device 126 may be irradiated with monochromatic incident electromagnetic radiation (not shown) having a wavelength in a range extending from about one-hundred (100) nanometers to about five-thousand (5,000) nanometers. At least a portion of the incident electromagnetic radiation may pass into the tunable resonant cavity 12. The tunable resonant cavity 12 may be tuned to resonate the incident electromagnetic radiation by selectively controlling the magnitude and polarity of the voltage $V_2$ applied between the first reflective member 14 and the second reflective member 16 until at least some of the incident electromagnetic radiation is resonating within the resonant cavity 12.

As previously discussed, at least some of the resonating incident electromagnetic radiation may pass through the second reflective member 16 and impinge on or irradiate the analyte. At least some of the incident electromagnetic radiation impinging on the analyte may be inelastically scattered by the analyte, thereby generating Raman-scattered radiation and a Raman signal. The Raman signal may be detected using an electromagnetic radiation detector (not shown) and used to identify, analyze, or otherwise characterize the analyte.

The Raman signal may be optimally enhanced by selectively controlling the magnitude and polarity of the voltage difference $V_1$ applied between the second layer of Raman signal-enhancing material 96 and the second reflective member 16, thereby selectively varying the distance between the second layer of Raman signal-enhancing material 96 and the second reflective member 16. This distance may be selected to optimally enhance the Raman signal emitted by the analyte, as previously discussed.

In this configuration, the Raman signal may be enhanced using both the tunable resonant cavity 12 and by providing a distance between the second reflective member 16 and the second layer of Raman signal-enhancing material 96 that can be selectively varied.

Raman devices and Raman signal-enhancing structures that embody teachings of the present invention may be used in Raman spectroscopy systems to perform Raman spectroscopy on an analyte.

Figure 9:
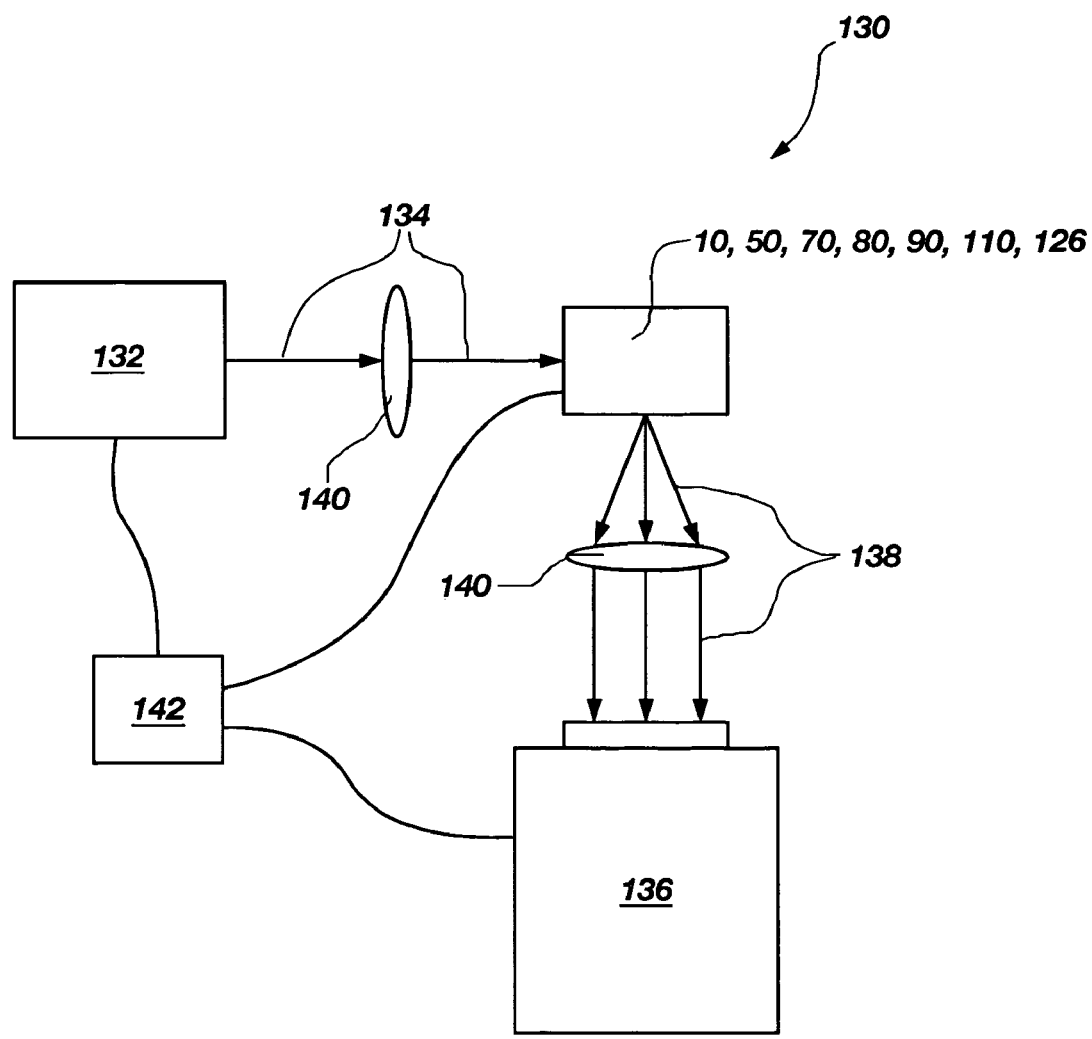
FIG. 9 is a schematic diagram of an embodiment of a Raman system of the present invention.

FIG. 9 is a schematic diagram of an exemplary Raman system 130 that embodies teachings of the present invention. The Raman system 130 includes an electromagnetic radiation source 132 that is configured to provide incident radiation 134 and an electromagnetic radiation detector 136 that is configured to detect Raman-scattered radiation 138 that is scattered by an analyte. The Raman system 130 also includes a Raman device or a Raman signal-enhancing structure that embodies teachings of the present invention. For example, the Raman system may include the Raman device 10, 126 or any one of the previously described Raman signal-enhancing structures 50, 70, 80, 90, 110. The Raman system 130 also may include various optical components 140 (such as, for example, apertures, lenses, and filters) positioned between the electromagnetic radiation source 132 and the Raman device or signal-enhancing structure 10, 50, 70, 80, 90, 110, 126 and between the Raman device or signal-enhancing structure and the radiation detector 136.

The radiation source 132 may include any suitable source for emitting incident electromagnetic radiation 134 at a desired wavelength and may be capable of emitting a tunable wavelength of monochromatic incident electromagnetic radiation 134. For example, commercially available semiconductor lasers, helium-neon lasers, carbon dioxide lasers, radiation emitting diodes, incandescent lamps, vertical cavity surface emitting lasers, edge emitting lasers, and many other known radiation emitting sources can be used as the electromagnetic radiation source 132. If necessary, a radiation filter may be used in conjunction with the electromagnetic radiation source 132 to provide monochromatic incident electromagnetic radiation 134. The wavelengths that are emitted by the electromagnetic radiation source 132 may be any suitable wavelength for performing Raman spectroscopy on the analyte, and may be within or near the visible region of the electromagnetic radiation spectrum.

The radiation detector 136 receives and detects the Raman-scattered radiation 138 that includes Raman-scattered photons that are scattered by an analyte located proximate the Raman device or signal-enhancing structure 10, 50, 70, 80, 90, 110, 126. The radiation detector 136 may include a device for determining the wavelength of the Raman-scattered radiation 138 and a device for determining the intensity of the Raman-scattered radiation 138. By way of example and not limitation, the radiation detector 136 may include a monochromator and a photomultiplier tube. As another example, the radiation detector 136 may include a wavelength dispersive grating and a charge coupled device. Typically, the Raman-scattered radiation 138 is scattered in all directions relative to the Raman signal-enhancing structure.

Optical components 140 positioned between the electromagnetic radiation source 132 and the Raman device or signal-enhancing structure 10, 50, 70, 80, 90, 110, 126 can be used to collimate, filter, or focus the incident electromagnetic radiation 134 before the incident electromagnetic radiation 134 impinges on the Raman device or signal-enhancing structure and the analyte. Optical components 140 positioned between the Raman device or signal-enhancing structure 10, 50, 70, 80, 90, 110, 126, and the radiation detector 136 can be used to collimate, filter, or focus the Raman-scattered radiation 138.

The Raman system 130 also may include a system controller 142 for controlling at least the radiation source 132 and the radiation detector 136. The system controller 142 also may be used to control a voltage applied to a Raman device or signal-enhancing structure. The system controller 142 may include an input system for allowing a user to control the operation of the components of the Raman system 130, and an output system for displaying or otherwise conveying information obtained from the Raman-scattered radiation 138. The system controller 142 may further include a computer devise including a signal processor and memory for collecting, storing, and otherwise manipulating data relating to the Raman signal obtained from the radiation detector 136.

It should be understood that Raman spectroscopy systems that embody teachings of the present invention may be provided in many forms, such as, for example, conventional table top systems or small portable Raman spectroscopy systems. For example, an exemplary Raman spectroscopy system that embodies teachings of the present invention may include a probe comprising one of the previously described Raman devices or signal-enhancing structures 10, 50, 70, 80, 90, 110, 126. Fiber optic cables or wires may be used to transport the incident electromagnetic radiation 134 from the radiation source 132 to the probe and to deliver Raman-scattered radiation 138 from the probe to the radiation detector 136. The radiation source 132, the radiation detector 136, and the system controller 142 may be provided in a single portable unit to provide a relatively small, portable Raman spectroscopy system.

The devices, structures, systems, and methods described herein may be used to improve the sensitivity of currently available Raman spectroscopy systems and to improve known techniques for performing Raman spectroscopy. The configuration of the devices and structures described herein can be formed by methods that involve the vertical construction, spacing, and positioning of elements or features that include a Raman signal-enhancing material. By enabling vertical construction of such elements or features, the spacing and location of the elements or features in Raman signal-enhancing structures can be more precisely controlled.

The Raman devices, signal-enhancing structures, and systems described herein may also be used to perform hyper-Raman spectroscopy and to enhance the hyper-Raman-scattered radiation.

The performance of molecular sensors, nanoscale electronics, optoelectronics, and other devices employing the Raman Effect may be improved by using Raman devices, Raman signal-enhancing structures, Raman systems, and methods that embody teachings of the present invention.

Although the foregoing description contains many specifics, these are not to be construed as limiting the scope of the present invention, but merely as providing certain representative embodiments. Similarly, other embodiments of the invention can be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

What is claimed is:

1. A Raman device comprising:
  a tunable resonant cavity comprising:
    a first reflective member;
    a second reflective member; and
    an electro-optic material disposed between the first reflective member and the second reflective member, the electro-optic material exhibiting a refractive index that varies in response to an applied electrical field; and
  a Raman signal-enhancing structure coupled to the tunable resonant cavity and configured to be irradiated by at least a portion of electromagnetic radiation that is resonating within the tunable resonant cavity.

2. The Raman device of claim 1, further comprising means for applying a voltage across the electro-optic material.

3. The Raman device of claim 1, wherein:
  the electro-optic material comprises a substantially planar layer of electro-optic material having a first major surface and a second major surface;
  the first reflective member comprises a substantially planar electrically conductive first layer of reflective material disposed on the first major surface of the layer of electro-optic material; and
  the second reflective member comprises a substantially planar electrically conductive second layer of reflective material disposed on the second major surface of the layer of electro-optic material, the second layer of reflective material comprising a Raman signal-enhancing material.

4. The Raman device of claim 3, wherein the Raman signal-enhancing structure coupled to the tunable resonant cavity comprises:
  the second layer of reflective material comprising a Raman signal-enhancing material; and
  a substantially planar additional layer of Raman signal-enhancing material oriented substantially parallel to the second layer of reflective material, at least a portion of the additional layer of Raman signal-enhancing material being separated from the second layer of reflective material by a distance of less than about fifty (50) nanometers.

5. The Raman device of claim 4, wherein the additional layer of Raman signal-enhancing material and the second layer of reflective material each comprise one of silver, copper, and gold.

6. The Raman device of claim 4, wherein the additional layer of Raman signal-enhancing material has a first major surface, a second major surface, and a plurality of apertures extending through the additional layer of Raman signal-enhancing material from the first major surface to the second major surface.

7. The Raman device of claim 6, wherein each aperture of the plurality of apertures has a substantially cylindrical shape and a diameter in a range from about ten (10) to about two-hundred (200) nanometers.

8. The Raman device of claim 6, wherein the apertures of the plurality of apertures are disposed in an ordered array.

9. The Raman device of claim 4, further comprising an analyte disposed between the at least a portion of the additional layer of Raman signal-enhancing material and the second layer of reflective material.

10. The Raman device of claim 9, further comprising a substantially monomolecular layer of molecules disposed between the at least a portion of the additional layer of Raman signal-enhancing material and the second layer of reflective material.

11. A Raman signal-enhancing structure comprising:
a substantially planar layer of Raman signal-enhancing material having a major surface;
a support structure extending from the major surface of the layer of Raman signal-enhancing material; and
a substantially planar member comprising a Raman signal-enhancing material disposed on an end of the support structure opposite the layer of Raman signal-enhancing material, the support structure separating at least a portion of the planar member from the layer of Raman signal-enhancing material by a selected distance of less than about fifty (50) nanometers.

12. The Raman signal-enhancing structure of claim 11, wherein the layer of Raman signal-enhancing material and the planar member each comprise one of silver, copper, and gold.

13. The Raman signal-enhancing structure of claim 12, wherein the support structure is substantially cylindrical and extends from the major surface of the layer of Raman signal-enhancing material.

14. The Raman signal-enhancing structure of claim 13, wherein the support structure comprises an elastically deformable material that is configured to elastically deform when a voltage is applied between the layer of Raman signal-enhancing material and the planar member.

15. The Raman signal-enhancing structure of claim 14, wherein the support structure comprises a piezoelectric material, the support structure being electrically coupled to the layer of Raman signal-enhancing material and to the planar member and configured to elastically deform when a voltage is applied between the layer of Raman signal-enhancing material and the planar member.

16. The Raman signal-enhancing structure of claim 13, wherein the planar member is disposed on an end of the support structure opposite the layer of Raman signal-enhancing material, at least a portion of the planar member extending laterally from the support structure to define a gap between a surface of the layer of Raman signal-enhancing material and at least a portion of a surface of the planar member.

17. The Raman signal-enhancing structure of claim 16, wherein the planar member is substantially cylindrical and has a diameter larger than a cross-sectional dimension of the support structure.

18. The Raman signal-enhancing structure of claim 11, wherein the planar member comprises a substantially planar discontinuous layer of Raman signal-enhancing material.

19. The Raman signal-enhancing structure of claim 18, wherein the discontinuous layer of Raman signal-enhancing material has a first major surface, a second major surface, and a plurality of apertures extending through the discontinuous layer of Raman signal-enhancing material from the first major surface to the second major surface.

20. The Raman signal-enhancing structure of claim 19, wherein each aperture of the plurality of apertures extending through the discontinuous layer of Raman signal-enhancing material is substantially cylindrical and has a diameter of less than about fifty (50) nanometers.

21. The Raman signal-enhancing structure of claim 20, wherein the support structure comprises a discontinuous layer of material disposed between the substantially planar layer of Raman signal-enhancing material and the substantially planar discontinuous layer of Raman signal-enhancing material.

22. The Raman signal-enhancing structure of claim 21, wherein the support structure comprises a plurality of isolated regions of support material.

23. The Raman signal-enhancing structure of claim 22, wherein each isolated region of the plurality of isolated regions of support material is substantially cylindrical and has a diameter of less than about 50 nanometers.

24. The Raman signal-enhancing structure of claim 21, wherein the support structure comprises a material configured to elastically deform when a voltage is applied between the layer of Raman signal-enhancing material and the planar member.

25. A Raman system comprising:
a radiation source configured to emit incident electromagnetic radiation;
a Raman device comprising:
a tunable resonant cavity comprising:
a first reflective member;
a second reflective member; and
an electro-optic material disposed between the first reflective member and the second reflective member, the electro-optic material exhibiting a refractive index that varies in response to an applied electrical field; and
a Raman signal-enhancing structure coupled to the tunable resonant cavity and configured to be irradiated by at least a portion of electromagnetic radiation that is resonating within the tunable resonant cavity; and
a radiation detector configured to detect Raman-scattered radiation that is scattered by an analyte.

* * * * *

UNITED STATES PATENT AND TRADEMARK OFFICE
CERTIFICATE OF CORRECTION

PATENT NO. : 7,359,048 B2  Page 1 of 1
APPLICATION NO. : 11/413910
DATED : April 15, 2008
INVENTOR(S) : Shih-Yuan Wang et al.

It is certified that error appears in the above-identified patent and that said Letters Patent is hereby corrected as shown below:

In column 7, line 60, delete "514" and insert -- 14 --, therefor

Signed and Sealed this

Fourteenth Day of July, 2009

JOHN DOLL
*Acting Director of the United States Patent and Trademark Office*